(12) United States Patent
Odrich et al.

(10) Patent No.: US 6,663,619 B2
(45) Date of Patent: Dec. 16, 2003

(54) METHOD AND SYSTEMS FOR LASER TREATMENT OF PRESBYOPIA USING OFFSET IMAGING

(75) Inventors: Marc Odrich, Riverdale, NY (US); Kenneth Greenberg, Ridgefield, CT (US); Jerome A. Legerton, San Diego, CA (US); Charles R. Munnerlyn, San Jose, CA (US); John K. Shimmick, Belmont, CA (US)

(73) Assignee: VISX Incorporated, Santa Clara, CA (US)

( * ) Notice: Subject to any disclaimer, the term of this patent is extended or adjusted under 35 U.S.C. 154(b) by 0 days.

(21) Appl. No.: 09/901,964

(22) Filed: Jul. 9, 2001

(65) Prior Publication Data

US 2001/0053906 A1 Dec. 20, 2001

Related U.S. Application Data

(62) Division of application No. 09/261,768, filed on Mar. 3, 1999, now Pat. No. 6,280,435.
(60) Provisional application No. 60/076,786, filed on Mar. 4, 1998.

(51) Int. Cl.⁷ .............................................. A61B 18/18
(52) U.S. Cl. ................................ 606/5; 606/4; 606/10; 351/212
(58) Field of Search ........................ 606/4–6, 10–12; 128/898; 351/212

(56) References Cited

U.S. PATENT DOCUMENTS

| | | | |
|---|---|---|---|
| 4,665,913 A | 5/1987 | L'Esperance, Jr. | |
| 4,669,466 A | 6/1987 | L'Esperance | |
| 4,732,148 A | 3/1988 | L'Esperance | |
| 4,770,172 A | 9/1988 | L'Esperance, Jr. | |
| 4,773,414 A | 9/1988 | L'Esperance, Jr. | |
| 5,163,934 A | * 11/1992 | Munnerlyn | ............... 606/5 |
| 5,296,881 A | 3/1994 | Freeman | |
| 5,314,422 A | 5/1994 | Nizzola | |
| 5,376,086 A | 12/1994 | Khoobehi et al. | |
| 5,395,356 A | * 3/1995 | King et al. | ............... 606/4 |
| 5,485,228 A | 1/1996 | Roffman et al. | |

(List continued on next page.)

FOREIGN PATENT DOCUMENTS

| | | |
|---|---|---|
| WO | WO 02/07660 A2 | 1/2002 |
| WO | WO 02/34178 A1 | 5/2002 |
| WO | WO 02/085231 A1 | 10/2002 |

OTHER PUBLICATIONS

Anschutz, T. (1994). "Laser correction of hyperopia and presbyopia," *Int. Ophthalmol Clin.* 34(4):107–137.

Josephson, J.E. (1993). "Corneal Bifocal Effects by Laser Photorefractive Keratectomy," *Arch Ophthalmol* vol. 111, pp. 582.

Shimmick, J., *Appendix A: VISX Myopie Corrections*, (1996) 1 page total.

Shimmick, J., *Appendix B: VISX Astigmatic Corrections*, (1997) 1 page total.

*Primary Examiner*—Roy D. Gibson
*Assistant Examiner*—Ahmed Farah
(74) *Attorney, Agent, or Firm*—Townsend and Townsend and Crew LLP; Lynn M. Thompson

(57) ABSTRACT

An ophthalmic surgery system and method for treating presbyopia by performing ablative photodecomposition of the corneal surface. A laser system ablates tissue to a predetermined ablation shape, and the cornea heals significantly to form a multifocal shape correcting presbyopia. The multifocal shape corrects for near-vision centrally and far-vision peripherally. The system and method enables wide area treatment with a laser having a narrower beam than the treatment area, and can be used in the treatment of many conditions in conjunction with presbyopia such as hyperopia, hyperopic astigmatism and irregular refractive aberrations.

35 Claims, 8 Drawing Sheets

U.S. PATENT DOCUMENTS

| | | | |
|---|---|---|---|
| 5,533,997 A | * | 7/1996 | Ruiz .............................. 606/5 |
| 5,556,395 A | | 9/1996 | Shimmick et al. |
| 5,574,518 A | | 11/1996 | Mercure |
| 5,683,379 A | | 11/1997 | Hohla |
| 5,803,923 A | * | 9/1998 | Singh-Derewa et al. ....... 606/5 |
| 5,827,264 A | | 10/1998 | Hohla |
| 5,835,192 A | | 11/1998 | Roffman et al. |
| 5,864,379 A | | 1/1999 | Dunn |
| 5,928,129 A | | 7/1999 | Ruiz |
| 6,019,754 A | * | 2/2000 | Kawesch ....................... 606/4 |
| 6,059,775 A | * | 5/2000 | Nielson ......................... 606/5 |
| 6,162,210 A | | 12/2000 | Shadduck |
| 6,245,059 B1 | * | 6/2001 | Clapman ....................... 606/5 |
| 6,258,082 B1 | | 7/2001 | Lin |
| 6,280,435 B1 | | 8/2001 | Odrich et al. |

* cited by examiner

METHOD AND SYSTEMS FOR LASER TREATMENT OF PRESBYOPIA USING OFFSET IMAGING

CROSS-REFERENCES TO RELATED APPLICATIONS

This application is a divisional application, and claims the benefit of priority from, U.S. patent application Ser. No. 09/261,768, filed Mar. 3, 1999, now U.S. Pat. No. 6,280,435, which is claims the benefit of prior Provisional Application No. 60/076,786, filed on Mar. 4, 1998 under 37 CFR §1.78(a), the full disclosures of which are hereby incorporated herein by reference.

STATEMENT AS TO RIGHTS TO INVENTIONS MADE UNDER FEDERALLY SPONSORED RESEARCH OR DEVELOPMENT

NOT APPLICABLE

REFERENCE TO A "SEQUENCE LISTING," A TABLE, OR A COMPUTER PROGRAM LISTING APPENDIX SUBMITTED ON A COMPACT DISK.

NOT APPLICABLE

BACKGROUND OF THE INVENTION

1. Field of the Invention

This invention relates to surgical modifications to the eye. In a specific embodiment, the invention provides ophthalmic surgery techniques which employ a laser to effect ablative photodecomposition of corneal tissue to correct presbyopia and/or other vision defects.

With aging, a condition of the eye known as presbyopia develops. With this condition, the crystalline lens of the eye loses the ability to focus on near objects when the eye is corrected for far-vision.

Presbyopia is often treated with bifocal eyeglasses. With bifocals, one portion of the lens is corrected for far-vision, and another portion of the lens is corrected for near-vision. By looking down through the bifocals, the user looks through the portion of the lens corrected for near-vision. When viewing distant objects, the user looks higher, through the portion of the bifocals corrected for far-vision.

Efforts have been made to treat presbyopia using partitioned lenses positioned directly over the pupil of the eye. Examples include multifocal contact lenses. Unfortunately, when presbyopia is corrected with bifocal or multifocal lenses attached to the cornea, the user is simultaneously looking through the near- and far-vision corrected lenses. As a result, the user will see both in-focus and out-of-focus images simultaneously when viewing an object. This out-of-focus image superimposed on the in-focus image can cause glare and degrade vision when viewing objects at low contrast.

Another technique for treating presbyopia has been to correct one eye of the patient for near-vision and to correct the other eye for distance-vision. This technique is known as monovision. With monovision, a patient uses one eye to see distant objects and the other eye to see close objects. Unfortunately with monovision, the patient may not clearly see objects that are intermediately positioned because the object is out-of-focus for both eyes. Also, a patient may have trouble seeing with only one eye.

Laser-based systems and methods are known for enabling ophthalmic surgery on the cornea in order to correct vision defects by the technique known as ablative photodecomposition. Changing the shape of the anterior surface of the cornea will change the optical properties of an eye. These ablative photodecomposition systems and methods control ultraviolet laser radiation flux density and exposure time upon the cornea so as to achieve a desired surface change in the cornea and thereby correct an optical defect.

Several different ablative photodecomposition techniques have been described to correct specific optical errors of the eye. For example, a myopic condition may be corrected by laser sculpting a corneal surface to reduce curvature. An astigmatic condition, which is typically characterized by a cylindrical component of curvature (departing from the otherwise generally spherical curvature of the cornea), can be corrected by a cylindrical ablation. Laser sculpting a corneal surface to increase the curvature can correct a hyperopic condition.

In a typical laser surgical procedure, the optically functional region of the corneal surface to be ablated is designated the optical zone. Depending on the nature of the desired optical correction, the optical zone may or may not be centered on the center of the pupil or on the apex of the anterior corneal surface. One technique for increasing the curvature of the optical zone for hyperopia error correction involves selectively varying the area of the cornea exposed to the laser beam radiation so as to produce an essentially spherical surface profile of increased curvature. This selective variation of the irradiated area may be accomplished in a variety of ways. For example, the optical zone can be scanned with a laser beam having a relatively small cross-sectional area (compared to the optical zone) in such a manner that the ablation depth increases with distance from the intended center of ablation. The result is a substantially spherical profile for the anterior corneal surface with maximum depth of cut at the extreme outer boundary of the optical zone. Another technique for sculpting the optical zone employs a rotatable mask having a plurality of apertures. The apertures are sequentially introduced into the laser beam path to provide progressive shaping of the laser beam in order to achieve the desired profile.

Efforts have also been made to treat presbyopia using ablative photodecomposition. One specific technique of treating presbyopia creates near-vision correction by ablating a region of the lower portion of the cornea adjacent the pupil rim. With this eccentric positioning of the ablation, the near-vision lens is not centered over the pupil. Consequently, constriction of the pupil may occlude the ablated near-vision lens. Constriction of the pupil is a natural response of the eye to illumination, and could potentially disrupt near-vision.

Alternative suggested presbyopia treatments include laser ablation of a small annular region of the cornea (having a diameter not exceeding 3.5 mm), or the ablation of a central lens for near-vision, surrounded by a gradual blend zone, and then a peripheral far-vision lens, all within the optically used portion of the cornea.

Efforts have been made in the past to laser sculpt a transition zone to provide a more gradual sloping of the walls and to eliminate the sharp discontinuity between the ablation zone and the surrounding untreated cornea. These efforts have included the use of a beam rotation or scanning mechanism operated by a computer to provide programmed ablation of the transition zone to achieve a sigmoid or other profile. While somewhat effective, these efforts often suffer from the added complexity of additional optical elements, such as a rotatable off-axis mirror or revolving prism having suitable optical properties.

2. Description of the Background Art

Systems and methods relevant to laser-based treatments for presbyopia are disclosed in the following U.S. patents and patent applications, the entire disclosures of which are hereby incorporated by reference: U.S. Pat. No. 5,395,356, issued Mar. 7, 1995, for "Correction of Presbyopia by Photorefractive Keratectomy"; U.S. Pat. No. 5,533,997, issued Jul. 9, 1996, "Apparatus and Method for Performing Presbyopia Correction"; and U.S. Pat. No. 5,314,422, issued May 24, 1994, for "Equipment for the Correction of Presbyopia by Remodeling the Corneal Surface by Means of Photoablation."

Ablative photodecomposition systems and methods are disclosed in the following U.S. patents and patent applications, the entire disclosures of which are hereby incorporated by reference: U.S. Pat. No. 4,665,913, issued May 19, 1987, for "Method for Ophthalmical Surgery"; U.S. Pat. No. 4,669,466, issued Jun. 2, 1987, for "Method and Apparatus for Analysis and Correction of Abnormal Refractive Errors of the Eye"; U.S. Pat. No. 4,732,148, issued Mar. 22, 1988, for "Method for Performing Ophthalmic Laser Surgery"; U.S. Pat. No. 4,770,172, issued Sep. 13, 1988, for "Method of Laser Sculpture of the Optically Used Portion of the Cornea"; U.S. Pat. No. 4,773,414, issued Sep. 27, 1988, for "Method of Laser Sculpture of the Optically Used Portion of the Cornea"; U.S. patent application Ser. No. 07/109,812, filed Oct. 16, 1987, for "Laser Surgery Method and Apparatus"; U.S. Pat. No. 5,163,934, issued Nov. 17, 1992, for "Photorefractive Keratectomy"; U.S. Pat. No. 5,556,395, issued Sep. 17, 1996, for "Method and System for Laser Treatment of Refractive Error Using an Offset Image of a Rotatable Mask"; U.S. patent application Ser. No. 08/368,799, filed Jan. 4, 1995, for "Method and Apparatus for Temporal and Spatial Beam Integration"; U.S. patent application Ser. No. 08/058,599, filed May 7, 1993, for "Method and System for Laser Treatment of Refractive Errors Using Offset Imaging"; U.S. Pat. No. 5,683,379, issued Nov. 4, 1997, for "Apparatus for Modifying the Surface of the Eye Through Large Beam Laser Polishing and Method of Controlling the Apparatus"; and U.S. Pat. No. 5,827,264, issued Oct. 27, 1998 for "Method of Controlling Apparatus for Modifying the Surface of the Eye Through Large Beam Laser Polishing."

Techniques for treating presbyopia with contact lenses are disclosed in the following U.S. patents and patent applications, the entire disclosures of which are hereby incorporated by reference: U.S. Pat. No. 5,835,192, issued Nov. 10, 1998, for "Contact Lens and Method of Fitting a Contact Lens"; U.S. Pat. No. 5,485,228 issued Jan. 16, 1996 for "Multifocal Ophthalmic Lens Pair;" and U.S. Pat. No. 5,864,379 issued Jan. 26, 1999 for "Contact Lens and Process for Fitting."

BRIEF SUMMARY OF THE INVENTION

It is an object of the invention to mitigate and/or inhibit presbyopia with minimal vision degradation by ablating a transition zone peripheral to an optical zone. It is a further object of the invention to ablate a cornea to produce a healed cornea with an aspheric optical zone that corrects presbyopia. In one aspect, the invention provides for ablating the cornea to a desired shape that compensates for changes in the corneal shape as the cornea heals. In another aspect, the invention provides for the simultaneous correction of presbyopic and other refractive corrections such as nearsightedness, farsightedness and astigmatism. In a yet further aspect, the invention provides for scaling the aspheric optical zone to match the size of the pupil. In yet another aspect, the invention provides for a method for treating presbyopia which includes ablating a transition zone outside an optical zone.

One of the major difficulties encountered in the application of laser surgery techniques to effect hyperopic and presbyopic refractive error corrections lies in the nature of the boundary between the optical zone and the untreated area. When the anterior surface of the cornea is sculpted to have an increased curvature, the maximum depth of cut occurs at the outer boundary of the optical zone. The generally annular region between this outer boundary and the adjacent untreated anterior surface portion of the cornea typically exhibits steep walls after the completion of the photoablation procedure. After the surgery, the eye tends to eliminate these steep walls with a stimulated healing response involving concurrent epithelial cell growth and stromal remodeling by the deposition of collagen, which results in corneal smoothing by filling in tissue in the steep walled region. This natural healing response acts to eliminate the discontinuity, resulting in a buildup of tissue in the steep walled region and over the outer portion of the optical zone. This natural phenomenon, sometimes termed the "hyperopic shift" in phototherapeutic keratectomy, causes a lack of precision for a given surgical procedure and diminished predictability, counteracting the beneficial effects of the refractive correction procedure and thereby reducing the desirability of the procedure to the prospective patient.

According to the present invention, the ablated surface can be contoured to provide an aspheric surface on a healed cornea. The invention provides for adjusting the ablation to compensate for factors effecting the final geometry of the healed cornea. These factors include corneal healing and the spatial variation of ablation. The shape of tissue ablated with a uniform laser beam pulse will depend upon the size and shape of the laser beam spot. The spatial variation of the total ablation may also cause variations in the ablated corneal shape. For example, a hyperopic ablation intended to produce a spherical ablation may demonstrate greater steepening near the center of the optical zone. This increased central curvature may form an aspheric surface that corrects for presbyopia.

The ablated surface is covered following the surgery, typically by a new epithelial layer or a repositioned anterior flap of the corneal tissue. Consequently, the final shape of the anterior surface of the cornea may be a different shape than the ablated shape. However, it is the final change in shape of the anterior surface of the cornea, not the initial ablated surface, which determines the refractive change effected by the surgery. Therefore, it may be desirable to ablate a shape on the cornea that is different from the final intended shape on the anterior surface of the cornea. For example, the optical zone may be ablated to a substantially spherical shape for correcting hyperopia. This ablated surface may then heal to an aspheric surface that corrects presbyopia.

The invention includes a method and system for performing ablative photodecomposition of the corneal surface that is capable of providing relatively smooth transition zones along with accurate sculpting of the anterior or other corneal surface to effect simultaneous symmetric or asymmetric refractive and presbyopic corrections with relatively large area coverage. The invention preferably employs a laser beam of smaller beam size than the total treatment area.

The invention further provides for the ablation of an optical zone that substantially matches the area of the pupil.

For presbyopic patients, the maximum pupil diameter is typically about 5 mm. Therefore, it is an aspect of the invention that the ablated optical zone have a diameter of about 5 mm, and be user selectable (by the user of the ablation system) to a diameter between 3 and 7 mm. The optical zone is preferably ablated to form a healed aspheric surface. Preferably, the central portion of the optical zone provides near-vision correction and the peripheral portion of the optical zone provides far-vision correction.

The invention additionally provides for scaling a diameter of the aspheric surface to the pupil. This scaling of the aspheric surface permits an appropriate balance between near and far-vision correction within the pupil. For example, a patient with a 5 mm diameter pupil may have a 2.5 mm diameter zone corrected for near-vision, while a patient with a 3 mm diameter pupil may have a 1.5 mm diameter zone corrected for near-vision. Scaling of the aspheric lens may be based on areas of the pupil and/or aspheric surface.

The invention also provides for ablating a transition zone peripheral to the optical zone and to the pupil. This positioning of the ablated transition zone will produce optimal results once the cornea heals. The ablated transition zone provides greater control over the healing process and provides greater control of the shape of the healed surface within the adjacent optical zone. Because the transition zone is ablated to control the shape of an adjacent healed surface, the transition zone may produce a corneal shape which corrects for neither near- nor far-vision. Thus, the transition zone is preferably positioned outside the pupil. Further, the transition zone is preferably sized so that healing of the cornea can be controlled within the adjacent optical zone. The optimal size of the transition zone is an annular region extending radially outward about 2 mm from the outer edge of the ablated optical zone. An ablation with a 5 mm diameter ablated optical zone and an optimally sized ablated transition zone will extend about 9 mm across the cornea. Transition zones of other sizes may be ablated outside the optical zone. Dimensions of the transition zone extending radially outward from the optical zone range from about 1 to 3 mm and preferably from about 1.5 to 2.5 mm.

In a first aspect, the present invention provides a method for reprofiling an anterior surface of the cornea of the eye. The anterior surface is reprofiled from an initial shape to a multifocal aspheric shape for correcting presbyopia. The method comprises aligning a laser system with the eye. The laser system is operable to deliver ablative radiation to the cornea. A surface of the cornea is ablated to a desired shape by selectively exposing the cornea to the ablative radiation. The cornea is ablated to an ablated shape so that an optical zone extends across the pupil and so that a transition zone is disposed beyond the pupil. The ablated surface is covered to produce a final aspheric anterior corneal surface.

In some embodiments, the covering step will comprise regenerating an epithelial layer over an ablated anterior surface of the cornea. In other embodiments, the covering step will comprise repositioning a flap of the cornea over the eye after a portion of either the flap, or the underlying corneal tissues, has been ablated.

In another aspect, the present invention provides an ophthalmic surgery system for performing selective ablation of a corneal surface of the eye so as to create a desired aspheric shape for correcting presbyopia on the anterior surface of a healed cornea. The system comprises means for directing a laser beam along a path. Means are also provided for profiling the beam to produce a profiled beam with a center. Means for displacing the center of the profiled beam over an area of the corneal surface will generally be coupled to the profiling means. A computer controls the positioning of the beam center over the area, and creates a plurality of successive laser beam pulses. The position of the plurality of pulses is determined by a laser treatment table that is scaled to a dimension of a pupil.

In another aspect, the present invention provides a laser eye surgery method comprising selectively ablating corneal tissue from an eye having an uncorrected surface shape. Corneal tissue is ablated so as to produce an initial ablated shape on an anterior surface of the cornea of the eye. The ablated eye heals, and the healed eye has a healed anterior surface shape which differs significantly from the initial ablated shape. This healed shape substantially, and in some instances entirely, corrects a refractive error of the eye.

In yet another aspect, the present invention provides a laser eye surgery method comprising selectively ablating corneal tissue from an eye having a refractive error. The refractive error is selected from the group consisting of myopia, hyperopia, and astigmatism. The ablating step removes a portion of cornea so as to simultaneously correct the refractive error and mitigate presbyopia of the eye.

In yet another aspect, the present invention provides a method for treating presbyopia of an eye. The eye has a pupil, and the method comprises selectively ablating corneal tissue from the eye so as to produce an ablated corneal surface. The corneal surface has an optical zone, and a transition zone surrounding the optical zone. The optical zone of the corneal surface defines an aspheric shape to mitigate the presbyopia, and a dimension of the optical zone substantially matches a dimension of the pupil under scotopic conditions.

In yet another aspect, the present invention provides a method for treating presbyopia of an eye. The eye has a pupil, and the method comprises selectively ablating corneal tissue from the eye so as to produce a corneal surface having an optical zone, and a transition zone surrounding the optical zone. The optical zone of the corneal surface defines an aspheric shape to mitigate the presbyopia. The transition zone is disposed outside of the pupil.

For a fuller understanding of the nature and advantages of the invention, reference should be had to the ensuing detailed description taken in conjunction with the accompanying drawings.

DETAILED DESCRIPTION OF THE INVENTION

Figure 1:
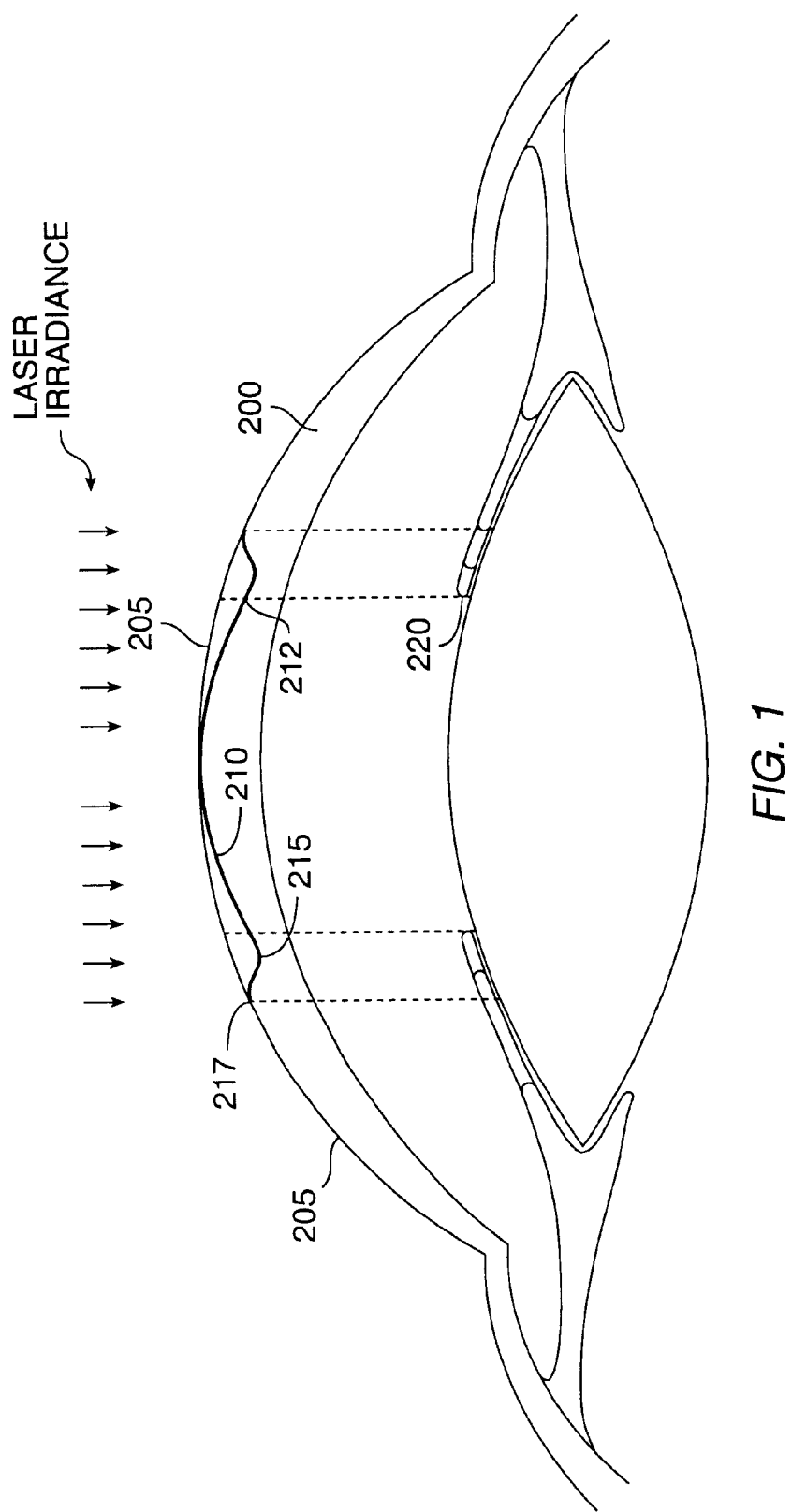
FIG. 1 is a side sectional view of an eye treated for presbyopia with the invention.

Turning now to the drawings, FIG. 1 illustrates a schematic side view of a cornea 200 treated with the invention. The cornea 200 has an anterior surface that provides most of the refractive power of the eye. The initial anterior surface 205 of the cornea 200 has been reshaped to a desired healed profile. The desired healed profile includes anterior optical surface 210 and anterior transition surface 215. The anterior optical surface 210 has a multifocal aspheric shape that corrects for near-vision centrally and far-vision peripherally.

While the present invention will often be described with reference to the mitigation of presbyopia in combination with refractive hyperopia treatment, it should be understood that the benefits of the present invention are not limited to these specific procedures. These presbyopia treatment techniques may be used when no other refractive correction (other than the correction, mitigation, and/or inhibition of presbyopia) is desired, or the present treatment may be combined with therapies for one or more of myopia, astigmatism, irregular refractive aberrations, and the like, as well as with hyperopia. Still other aspects of the present invention, including methods and systems which accommodate and adjust for re-epithelization, may find uses in a broad variety of ophthalmic procedures.

The peripheral positioning of the far-vision correction advantageously permit distance viewing when the pupil is dilated at night. Anterior transition surface 215 is the anterior surface of the cornea that provides a gradual change in shape between anterior optical surface 210 and the portion of the cornea retaining the initial anterior surface 205. The outer boundary 212 of the anterior optical surface preferably extends entirely across, and is ideally substantially coextensive with, the pupil which is bounded by iris 220. The light rays passing through anterior transition surface 215 do not contribute to the image formed by anterior optical surface 210. Therefore, anterior transition surface 215 is desirably positioned outside the pupil. This positioning of anterior transition surface 215 causes the light rays passing through anterior transition surface 215 to be substantially occluded by iris 220. This occlusion improves patient vision because the light rays are blocked that do not contribute to image formation, and which would otherwise reduce the contrast of the image.

The optical correction effected by an ablative surgical procedure to the cornea is derived from a change in the anterior corneal surface from an initial anterior surface 205 to post-operative anterior optical surface 210. The anterior optical correction is the post-operative anterior optical surface 210 minus the initial anterior surface 205. An ablation profile is a change in an exposed surface profile occurring immediately after the tissue removal process. Therefore, the ablation profile is the exposed surface profile immediately after the tissue removal process minus the initial exposed surface profile. As used herein, "ablated shape" can refer either to an ablation-induced change in a surface topography on a surface of the cornea, or to the surface topography of the cornea after ablation. Similarly, "healed shape" can mean either a final corneal topography once healing is complete, or a change in the corneal topography from an initial topography to a final corneal topography once healing is complete. A healed shape differs significantly from an ablated shape when a difference between the two shapes is sufficient to be perceptible by a patient. Healing can refer either to an initial covering of an ablated surface contour or changes in a tissue structure of the cornea following an initial covering of an ablated surface contour.

Figure 2:
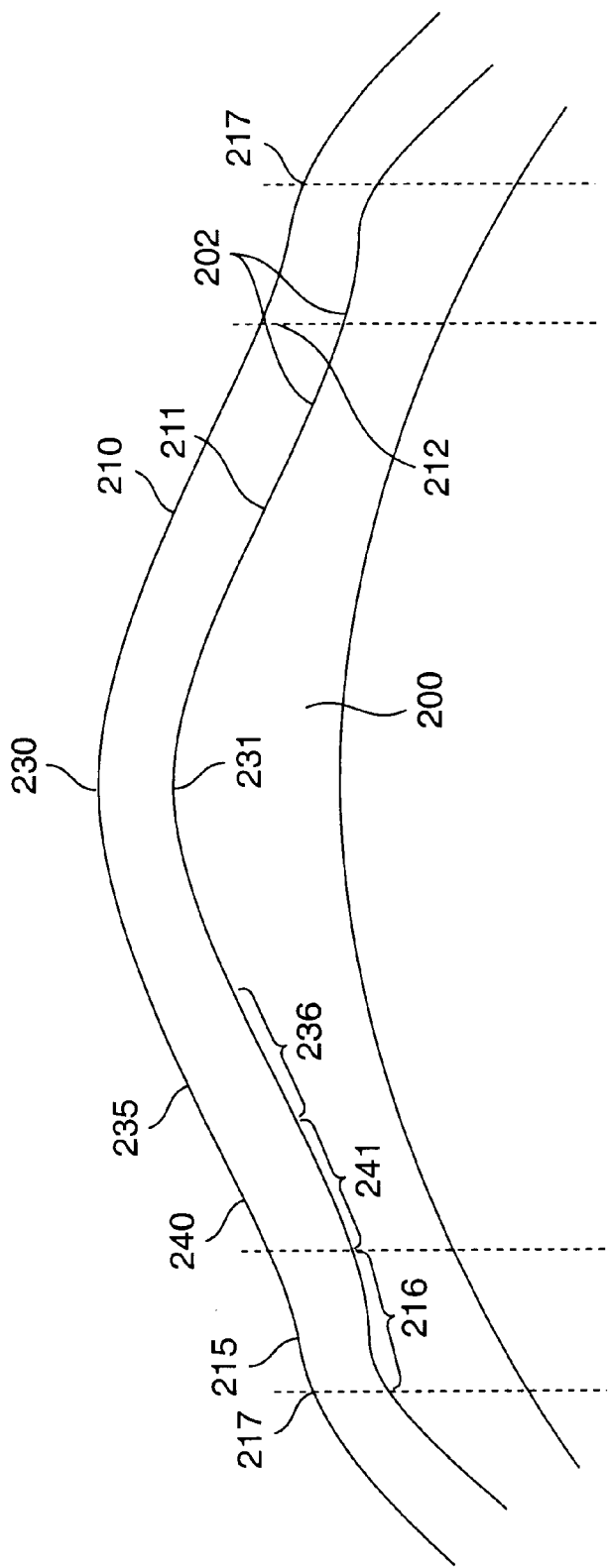
FIG. 2 is a side sectional view of an ablation profile illustrating the effect of corneal healing on ablation shape.

The relationship of the ablated surface and the anterior corneal surface overlying the ablated surface is shown in FIG. 2. Initial ablated surface 202 includes ablated optical zone 211 and ablated transition zone 216. Ablated optical zone 211 includes ablated central optical zone 231 for the correction of near-vision, ablated peripheral optical zone 241 for the correction of far-vision, and ablated intermediate optical zone 236 for the correction of vision intermediate to near- and far-vision. Ablated central optical zone 231 is shaped to appropriately form anterior central optical surface 230 when ablated surface 202 is covered and cornea 200 is healed to form anterior optical surface 210. Ablated intermediate optical zone 236 is shaped to form anterior intermediate optical surface 235 when ablated surface 202 is covered and cornea 200 is healed. Ablated peripheral optical zone 241 is shaped to appropriately form anterior peripheral optical surface 240 when ablated surface 202 is covered and cornea 200 is healed. Ablated transition zone 216 is ablated to minimize the effect of corneal healing on anterior optical surface 210.

In one embodiment, covering of the ablated shape will cause the final shape of anterior optical surface 210 of the anterior surface of cornea 200 to be different from ablated optical zone 211. This aspect of the present invention is more fully described in the publication entitled "Corneal Ablation Profilometry and Steep Central Islands," Journal of Refractive Surgery, Vol. 13, pp. 235–45, 1997, the entire disclosure of which is herein incorporated by reference.

Initial ablated shape 202 is covered after the ablation. Proximity to ablated transition zone 216 may cause anterior peripheral optical surface 240 to be a different shape than underlying ablated peripheral optical zone 241. However, anterior central optical surface 230 of anterior optical surface 210 is distant from ablated transition zone 216. Therefore the shape of anterior central optical surface 230 will more closely match the shape of ablated central optical zone 231. In one aspect, the covering may include regeneration of the epithelial layer following ablation of Bowman's membrane and adjacent stromal layers. In another aspect, covering includes replacing a resected portion of the cornea as is described in U.S. Pat. No. 4,903,695, issued Feb. 27, 1990, for "Method and Apparatus for Performing a Keratomileusis or the Like Operation." In this aspect, the resected portion includes an epithelial layer. In a yet further aspect of covering, a tear film forms over the epithelial layer to form the anterior surface when cornea 200 is fully healed. The final shape of anterior optical surface 210 will substantially determine the optical properties of the cornea. Therefore, it may be desirable to ablate cornea 200 to form ablated optical zone 211 that is a different shape than the shape of anterior optical surface 210.

In another embodiment, ablated optical zone 211 includes ablated central optical zone 231 and ablated peripheral optical zone 241. Ablated intermediate optical zone 241 may be replaced by extending ablated peripheral optical zone 241 and ablated central optical zone 231 to border one another. Ablated central optical zone 231 provides about 2.5 D of near-vision correction with a range from about 0.5 to 4 D, preferably about 2 to 3 D and a diameter from about 1.0 to 3.5 mm and preferably from about 2 to 3 mm. Ablated peripheral optical zone 241 is ablated to provide far-vision correction and is sized to extend radially outward from the outer boundary of ablated central optical zone 231 to a diameter of about 5 mm with a range from about 3 to 7 mm and preferably from about 4 to 6 mm. Ablated transition zone 216 extends radially outward from the outer boundary of ablated optical zone 211 to a diameter of about 9 mm with a range from about 6 to 11 mm and preferably from about 7 to 10 mm. Covering of ablated optical zone 211 will cause anterior intermediate optical surface 240 to form over the border between ablated central optical zone 231 and ablated peripheral optical zone 241. Anterior central optical surface 230 will form over ablated central optical zone 231. Anterior peripheral optical surface 240 will form over ablated peripheral optical zone 241. Therefore, anterior optical surface 210 may be formed as a multifocal aspheric surface on cornea 200 by ablating only two optical zones within ablated optical zone 211.

Figure 3:
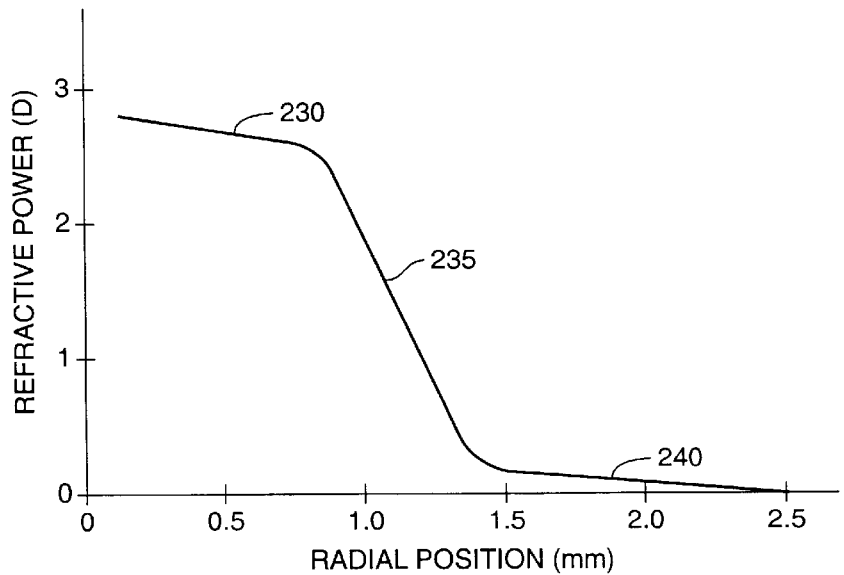
FIG. 3 illustrates the refractive power over the pupil of an aspheric surface for treating presbyopia.

An illustrative plot of the relative refractive power of anterior optical surface 210 as a function of radial position across the pupil is shown in FIG. 3. The refractive power decreases from the center toward the periphery. Anterior central optical surface 230 of cornea 200 has a relative refractive power from about 1 to 4 D, and preferably from about 2 and 3 D that corrects for near-vision. This central surface ranges from about 1 to 3 mm in diameter and preferably from about 1.5 to 2.5 mm in diameter. Anterior peripheral optical surface 240 corrects for far-vision. This peripheral surface has an inner boundary from about 2 and 4 mm in diameter and an outer boundary 212 that may be scaled to match the outer boundary of the pupil as shown in FIG. 1. Outer boundary 212 may be scaled to a diameter of between about 3 and 7 mm. Anterior intermediate optical surface 235 has continuously varying refractive power. This region is desirable and provides focus for objects appropriately positioned intermediate to near and far positions.

In an exemplary embodiment, ablated central optical zone 231, ablated intermediate optical zone, 236 and ablated peripheral optical zone 241 are scaled to match a dimension of the pupil. The scaling dimensions may be an area of the pupil, a diameter of the pupil, a radius, or the like. For example, ablated optical zone 211 may be decreased by about 20% from a diameter of about 5 mm to 4 mm for a patient with a 4 mm diameter pupil. In this case, ablated central optical zone 231, ablated intermediate optical zone 236 and ablated peripheral optical zone 241 are each decreased by about 20%. This scaling is desirable because it keeps the ratios of near, intermediate and far-vision nearly constant for varying pupil size. The inner boundary of ablated transition zone 216 is scaled to border the outer boundary of ablated optical zone 211. During the scaling of ablated optical zone 211, the outer boundary of ablated transition zone 216 may be scaled to match the scaling of ablated optical zone 211. Alternatively, the outer boundary of ablated transition zone 216 may be fixed to a constant value while the inner boundary of ablated transition zone 216 is varied.

Figure 4:
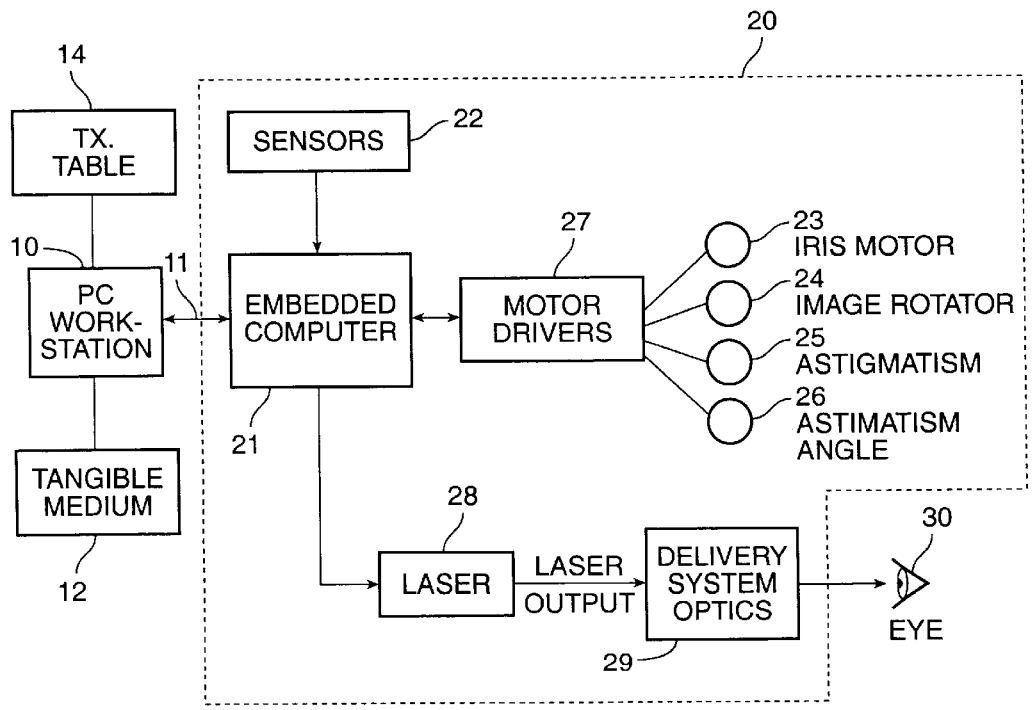
FIG. 4 is a block diagram of an ophthalmic surgery system for incorporating the invention.

FIG. 4 illustrates a block diagram of an ophthalmic surgery system for incorporating the invention. As seen in this Figure, a personal computer (PC) work station 10 is coupled to an embedded computer 21 of a laser surgery unit 20 by means of a first bus connection 11. The PC work station 10 comprises a tangible medium 12 and a treatment table 14. The laser treatment table 14 includes a listing of coordinate references of the laser beam during an ablation of the cornea. The sub-components of laser surgery unit 20 are known components and preferably comprise the elements of the VISX STAR™ EXCIMER LASER SYSTEM and of the STAR S2™ System available from VISX, Incorporated of Santa Clara, Calif. Thus, the laser surgery system 20 includes a plurality of sensors generally designated with reference numeral 22 which produce feedback signals from the movable mechanical and optical components in the laser optical system, such as the elements driven by an iris motor 23, an image rotator 24, an astigmatism motor 25 and an astigmatism angle motor 26. The feedback signals from sensors 22 are provided via appropriate signal conductors to the embedded computer 21. The embedded computer 21 controls the operation of the motor drivers generally designated with reference numeral 27 for operating the elements 23–26. In addition, embedded computer 21 controls the operation of the excimer laser 28, which is preferably an argon-fluorine laser with a 193 nanometer wavelength output designed to provide feedback stabilized fluence of 160 mJoules per square centimeter at the cornea of the patient's eye 30 via the delivery system optics generally designated with reference numeral 29 and shown in FIG. 9. Other lasers having a suitable wavelength may be used to make an ablative energy for removing a tissue from the eye. For example, solid state lasers such as a yttrium aluminum garnet (YAG) laser producing a fifth harmonic of a fundamental wavelength may be used to generate an ablative energy. Other ancillary components of the laser surgery system 20 which are not necessary to an understanding of the invention, such as a high resolution microscope, a video monitor for the microscope, a patient eye retention system, and an ablation effluent evacuator/filter, as well as the gas delivery system, have been omitted to avoid prolixity. Similarly, the keyboard, display, and conventional PC subsystem components (e.g., flexible and hard disk drives, memory boards and the like) have been omitted from the depiction of the PC work station 10. If desired, embedded computer 21 may be constructed with PC work station components and built into laser surgery system 20. In this case embedded computer 21 may supplant PC workstation 10.

Figure 5:
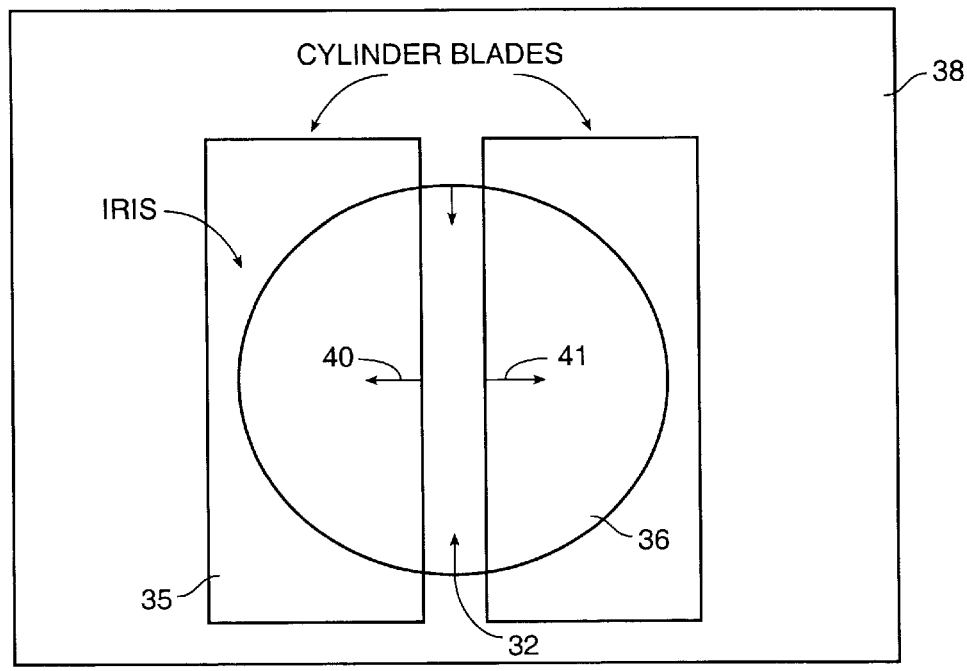
FIG. 5 is a schematic plan view illustrating a movable slit and variable diameter aperture used in the system 20 of FIG. 4.

The iris motor 23 is used to control the diameter of a variable diameter iris schematically depicted in FIG. 5. The astigmatism motor 25 is used to control the separation distance between a pair of cylinder blades 35, 36 which are mounted on a platform 38 for bi-directional translational motion in the direction of arrows 40, 41. Platform 38 is rotatably mounted on a second platform (not illustrated) and is rotationally driven by astigmatism angle motor 26 in a conventional way in order to enable alignment of the slit axis (illustrated in a vertical orientation in FIG. 5) with the appropriate coordinate axes of the patient's eye. Iris 32 is driven by iris motor 23 in a known way to change the diameter of the iris opening from a fully opened position (the position illustrated in FIG. 5) to a fully closed position in which the aperture is closed to a minimum diameter of 0.8 mm. It is understood that the variable diameter iris 32 and the cylinder blades 35, 36 are positioned with respect to the output of laser 28 in such a manner as to intercept the beam prior to irradiation of the corneal surface of the patient's eye 30. For the purpose of this application, it may be assumed that iris 32 and cylinder blades 35, 36 are part of the delivery system optics subunit 29 shown in FIG. 4.

The system of FIGS. 4 and 5 is used according to the invention to effect presbyopic, hyperopic, myopic, astigmatic, and other error corrections to the anterior surface of the cornea, to provide a smooth transition zone between the outer edge of the optical zone and the untreated surface of the cornea, and to effect surface smoothing when desired. Other techniques besides the above area profiling of a laser beam may be used to profile the laser beam to a desired size and energy distribution on the surface of the eye. For example a lens may be used to profile a beam exiting from an aperture by focusing the beam to a suitably small area and desired energy profile as described in U.S. Pat. No. 4,718, 418, the full disclosure of which is herein incorporated by reference. Also a diffractive optic may be used to adjust an energy profile of the laser beam on the surface of the eye as described in co-pending application entitled Laser Delivery System and Method with Diffractive Optic Beam Integration, U.S. patent application Ser. No. 09/015,841 filed on Jan. 29, 1998 the full disclosure of which is herein incorporated by reference.

Figure 6:
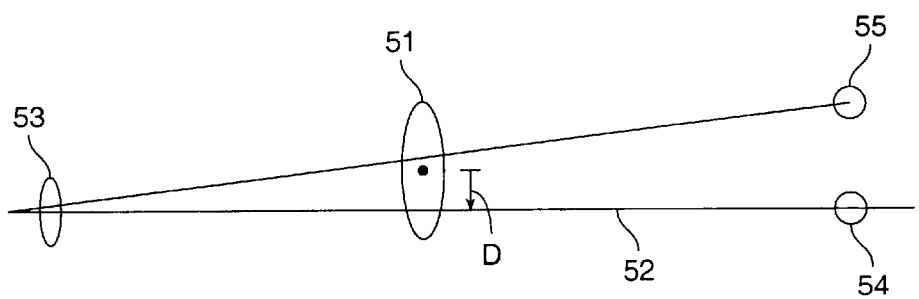
FIG. 6 is a schematic diagram illustrating the offset lens principle.
Figure 7:
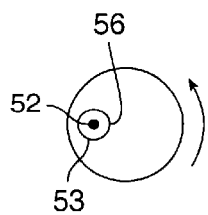
FIG. 7 is a schematic diagram illustrating the lens offset viewed along the axis of rotation.

With reference to FIG. 6, an imaging lens 51 is laterally offset from an axis 52 by a variable amount in the manner set forth more fully below. Lens 51 preferably comprises the existing imaging lens found in the delivery system optics 29 of the FIG. 4 system. Axis 52 is the axis corresponding to the center of rotation of lens 51. Displacing lens 51 by translating the lens in a radial direction off the axis 52, which may or may not correspond to the laser beam axis, displaces the image 54 of aperture 53 in a related manner. By also rotating lens 51 about the axis 52 in an eccentric fashion, as illustrated in FIG. 7, the displaced image 54 of aperture 53 can be scanned about axis 52. This scanning is along a preselected path, which in the hyperopic correction procedure described below is an annular path about the axis 52. Depending upon the manner in which the lens offset, lens rotation, slit width, slit rotation and iris diameter are controlled, various types of ablation corrections can be effected. These corrections include presbyopia correction, hyperopic error corrections, hyperopic astigmatism corrections, and other vision error corrections, along with simultaneous or successive edge contouring to form a smooth transition zone.

Figure 8:
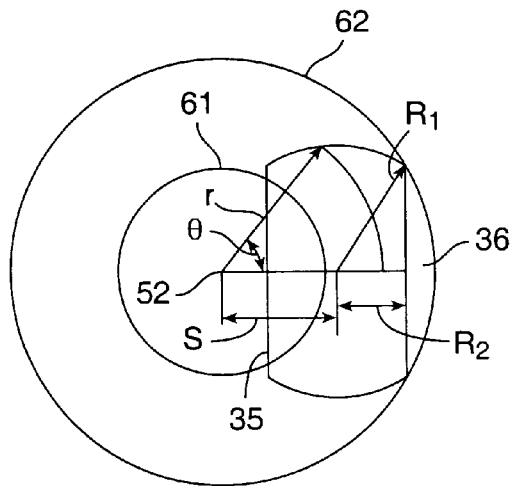
FIG. 8 is a schematic view showing the ablation geometry for the aperture of FIG. 5.

FIG. 8 illustrates the aperture positioning relative to the intended ablation center when employing the variable diameter iris 32 and cylinder blades 35, 36 of FIG. 5 to effect a refractive error correction. In this Figure, R2 represents the half width of the slit between blades 35, 36, Ri is the radius of the iris 32, r is the radius of a circle covered by the aperture, s is the radial offset of the center of the image of the slit aperture relative to the center of rotation 52, and 0 is the half angle for which the circle of radius r is covered by the aperture. The intended ablated optical zone is the central region bounded by circle 61 and the intended ablated transition zone is the annular region bounded by circles 61 and 62.

The manner in which the slit width and diameter are varied by the computer depends upon the type of vision correction desired. For a hyperopic correction, a fixed value of the refractive correction may be used to generate the cut profile C(r). For a hyperopic refractive correction of a given fixed value, the sequencing of the aperture is done in such a manner as to satisfy the hyperopic lens equations described in "Photorefractive Keratectomy: A Technique for Laser Refractive Surgery" authored by Munnerlyn et al., J. Cataract Refract. Surg. Vol. 18, pages 46–52 (January, 1988), the entire disclosure of which is hereby incorporated by reference. Also, European Patent Office publication number EP 0 628 298 A1, published Dec. 14, 1994, discloses an aperture sequencing for correcting hyperopia, the entire disclosure of which is hereby incorporated by reference.

For the correction of presbyopia, it may be desirable to vary the refractive power across the ablated surface. The cut profile C(r) may be calculated by calculating the incremental cut profiles along the surface. The incremental cut profiles are then summed to calculate the overall cut profile C(r). The incremental cut profiles may be calculated using the above hyperopic lens equation, the desired ablated refractive correction, and the position from the center of the aspheric lens.

The cut profile is given by the equation:

$$C(r) = (d/\pi) \Sigma_i (n_i \theta(r)) \tag{1}$$

where $n_i$ is the number of laser pulses for the $i^{th}$ aperture in a sequence of aperture dimensions and radial positions, and d is the amount of material removed with each laser pulse or a scaling factor which also takes into account corneal healing. Once the cut profile has been calculated, the sequence of aperture dimensions and pulses may be calculated. The sequence of aperture dimensions is created by control of the width of the slit and the diameter of iris 32 throughout the surgical procedure. The sequence of aperture dimensions and positions are preferably incorporated into a laser treatment table.

The sequence of aperture dimensions may also be tailored to accommodate variations in the ablation profiles of individual pulses from the laser beam. For example, the spatial variation of tissue ablation may cause the geometry of tissue ablated with a single laser pulse to be deeper at the edges of an ablation adjacent the image of iris 32 and cylinder blades 35 and 36. For an individual laser pulse, this increased ablation depth near the edge of an ablation may be 50% greater than the central ablation depth. Therefore, a 4D intended hyperopic ablation that assumes a uniform layer of tissue is removed with each laser pulse will ablate about 6 D of correction near the center of ablated optical zone 211. Clinically, the inventors have observed that patients treated with the above ablation algorithm for 3 to 4 D of hyperopia have also been successfully treated for presbyopia. However, with a +2D correction, the correction of presbyopia is only partial. Therefore to correct presbyopia and hyperopia, it may be desirable to combine the +2 D correction with an aspheric ablation. In this case, the aspheric correction is about one half of the aspheric correction that would be ablated on an eye with no refractive error.

Preferably, the refractive correction of cut profile C(r) is scaled to match a dimension of the pupil. This scaling may be achieved by appropriately varying the refractive correction entered into the hyperopic lens equation. For example, consider the scaling of an ablation for a 5 mm pupil compared to a 4 mm pupil. If the aspheric surface includes a 1.5D ablated curvature 1.25 mm from the aspheric lens center for the 5 mm pupil, this 1.5D curvature will be ablated 1.0 mm from the aspheric lens center on a 4 mm pupil. This scaling maintains a balance of near and far-vision correction by accommodating individual variability in pupil size. By scaling the cut profile C(r), the scaling of the ablated optical zone is incorporated into the laser treatment table.

For the example shown in FIG. 8, the values of s and R2 are varied to produce the correct value of radial offset (s) and slit width (2×R2) so that the inner edge of blade 35 is moved in steps from close to the center of the ablation (starting at approximately 0.6 mm from the center) to the edge of the corrected optical zone at approximately 2.5 mm. R, (the iris radius) is fixed at a predetermined value (3 m in one specific procedure), and s and R2 are chosen to anchor the edge of the ablation at the outer edge of the intended transition zone of approximately 5 mm radius. The number of pulses for each successive position of the inner edge is calculated to give the desired depth from the hyperopic lens equation. For a procedure requiring the least number of pulses, the treatment is ended as soon as the inner edge of the aperture reaches the boundary of the corrected optical zone. Initially, the slit width is set to a maximum value and the imaging lens 51 is positioned laterally of the axis of rotation 52 such that the inner slit edge is positioned at the minimum distance from the center of the optical zone and the intersections of the iris diaphragm 32 and the outer slit edge are positioned over the outer edge of the intended transition zone.

The image of the aperture is now ready to be scanned over the anterior surface of the cornea. While several different scanning sequences are possible, the following sequence has been actually implemented with effective results. The radial position along the optical zone is broken into a series of discrete, equidistant (typically 0.1 mm apart) nodes. The number of pulses required to ablate tissue to cut depth $C(r)$ at a node adjacent to the edge of the inner slit is calculated using $$n = (\pi * \delta C(r_n) / \theta_i(r_n) * d)$$

where n is the number of pulses, $\delta C(r_n)$ is the difference between the actual ablation depth from previous pulses and the desired ablation depth at the node, $\theta_i(r_n)$ is the half angle coverage of the aperture at $r_n$ as previously defined. The radial ablation profile from previous pulses is calculated by summing the ablation depth from previous positions and pulses at each node as described by equation I. For the initial position, $\delta C(r_n) = C(r)$. The number of pulses required for each subsequent node is calculated for each node adjacent to the inner cylinder blade as the blade moves toward the edge of the optical zone. Having determined the correct number of pulses at each node, the treatment must be smoothed rotationally to ensure that it is correct and free from aberrations.

Figure 9:
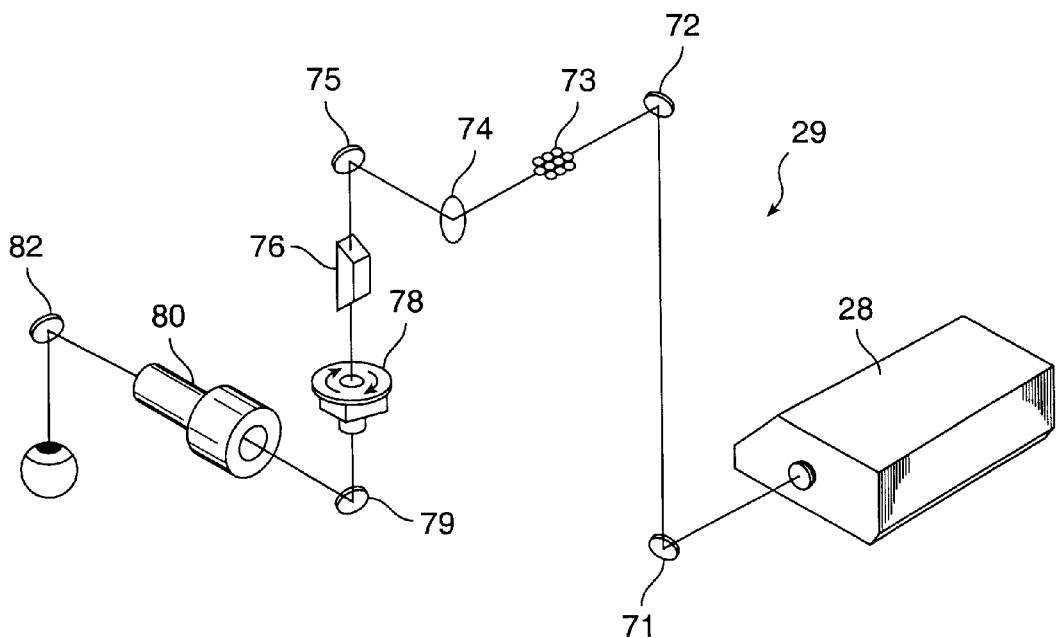
FIG. 9 is a schematic view of the delivery system optics.

FIG. 9 is a schematic view of the delivery system optics in an embodiment. As seen in this Fig., the beam from laser 28 is reflected by a first mirror 71 and a second mirror 72, and enters a spatial integrator 73, where the beam is modified in cross-section. A diffractive optic may be used to modify a cross section of the laser beam as described in co-pending application entitled Laser Delivery System and Method with Diffractive Optic Beam Integration, U.S. patent application Ser. No. 09/015,841 filed on Jan. 29, 1998, the full disclosure of which is incorporated herein by reference. The modified beam exiting from spatial integrator 73 is reflected by mirrors 74 and 75 and passed through a dove prism 76 to the iris/slit mechanism 78 which contains the variable width slit and variable diameter iris described above. The profiled beam exiting from the unit 78 is reflected by a mirror 79 and enters the image offset control unit 80 which contains imaging lens 51. The offset profiled image exiting from unit 80 is reflected from a mirror 82 onto the patient's eye. To smooth out fluctuations in beam energy across the beam area, dove prism 76 is rotatably mounted, and is typically rotated during beam generation either continuously or between pulses.

The invention affords great flexibility in performing various types of corrections by virtue of the fact that the system can be programmed to accommodate patients having differently sized physical eye parameters and refractive and presbyopic correction requirements. The variable slit width/variable diameter iris arrangement is particularly adaptable for use in the simultaneous treatment of presbyopia, hyperopia, hyperopic astigmatism and irregular refractive aberrations. For simultaneous treatment of presbyopia, hyperopia and hyperopic astigmatism, the ablation geometry is solved as a function of radial displacement and angular position of the aperture image about the rotational center. Further, in all procedures requiring a smoothing of the transition zone at the periphery of the ablation zone, the diameter of the iris is varied over a predetermined range along with the slit width variation. For presbyopia and refractive aberrations, a device such as a spatially resolved refractometer or a topography machine or both may be used to map the irregular surface contour of the cornea to determine the exact surface corrections required. Thereafter, the slit width and the iris diameter can be programmed such that corneal sculpting will achieve the desired aspheric surface geometry on a healed cornea. Alternatively, a wavefront sensor may be used to map the irregular refractive aberrations of the eye. One suitable embodiment of such a wavefront sensor is the Hartmann-Shack sensor described in U.S. Pat. No. 5,777,719, the entire disclosure of which is herein incorporated by reference.

For any of the above specific correction procedures, a treatment table is normally constructed. The treatment table contains the value of all of the discrete radial and angular positions of the optomechanical elements used to scan the image over the relevant portion of the anterior corneal surface. This table also contains the number of laser pulses per position. A typical treatment table contains on the order of about 500 different entries.

The treatment table for a given procedure may incorporate special features designed to improve the efficiency of the procedure. For example, for some procedures (e.g., simultaneous hyperopic and presbyopic correction) it can be beneficial to leave a small zone centered on the optical zone untreated. This can be done by constraining motion of the inner cylinder blade to guarantee occlusion in the small zone of interest. The diameter of the untreated zone varies from about 0.1 to 1.5 mm, is preferably from about 0.5 to 1.0 mm and is ideally about 0.7 to 0.9 mm. Also, standard tables can be constructed for a specific procedure-e.g., hyperopic correction—to different Dioptric correction values, and these standard tables can be sorted and combined to perform multiple repetitions of one or more standard tables to effect a given Dioptric correction. For example, standard tables may be created for a myopic correction for values of ¼, ½ and 1 Diopter. Using these tables, a 3.75 Diopter correction would proceed by performing the standard 1 Diopter correction three times, followed by the ½ Diopter correction and the ¼ Diopter correction.

While the invention has been described above with specific reference to ablation of an anterior corneal surface, various portions of the cornea may also be treated using the invention. For example, the epithelium may be mechanically removed by scraping, as is typically done in photorefractive keratectomy, and the exposed surface may be ablated. Further, the invention can also be used for laser keratomileusis of corneal lamella removed from the cornea. This procedure is described in U.S. Pat. No. 4,903,695, issued Feb. 27, 1990, for "Method and Apparatus for Performing a Keratomileusis or the Like Operation."

In applying the invention to this procedure, a flap of corneal tissue is physically removed (either fully or partially) from the cornea, the size of the removed portion typically lying in the range from about 8 to 10 mm wide and a variable thickness up to 400 microns. This flap of tissue is typically removed using a microkeratome. Next, the flap is placed in a suitable fixture—typically an element having a concave surface—with the anterior surface face down. Thereafter, the required ablation is performed on the reverse exposed surface of the flap, after which the ablated flap is repositioned on the cornea. Alternatively, after the flap is removed from the cornea, the exposed stromal tissue of the eye can be ablated according to the invention, after which the flap is reattached over the freshly ablated stromal tissue.

Figure 10:
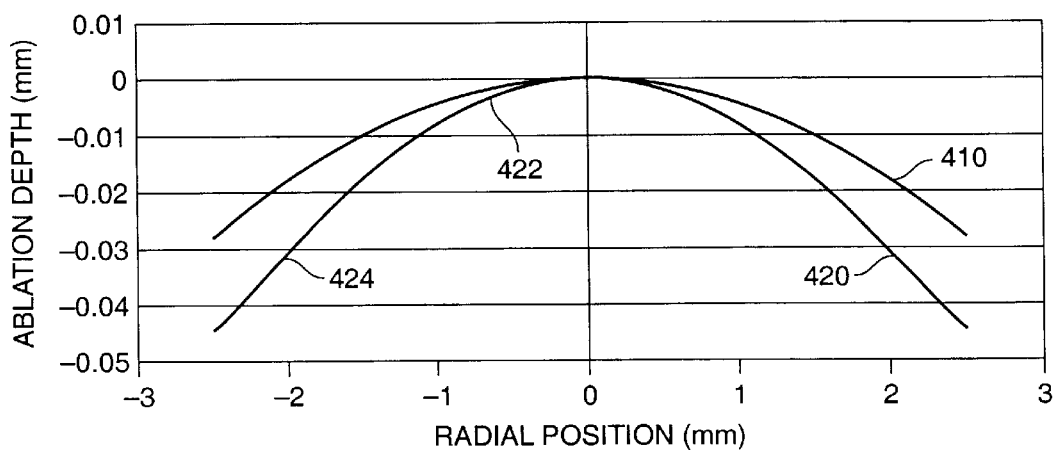
FIG. 10 illustrates an ablation profile on a corneal surface in comparison to an intended +3 D spherical optical correction.

The technique of shaping a cornea is further illustrated in FIGS. 10–15. These figures illustrate measured ablation profiles, intended optical corrections and measured anterior corneal surface optical corrections. The effect of the spatial variance of ablation on ablation shape is illustrated in FIG. 10. A measured ablation shape is plotted as a function of radial position over the ablated optical zone. This figure illustrates an ablated optical zone using an ablation algorithm that assumes a uniform layer of tissue is removed with each laser beam pulse. The intended optical correction is a +3 D optical correction 410. However, illustrated ablated optical zone 420 is significantly different. The ablated optical zone 420 is overcorrected by about 100% in the central ablation zone 422. The ablated optical zone 420 is over corrected in the peripheral ablation zone 424 by about 60%. The initial shape of ablated optical zone 420 differs significantly from the healed anterior surface shape, and the healed shape substantially corrects the initial hyperopic refractive error of the eye.

Figure 11:
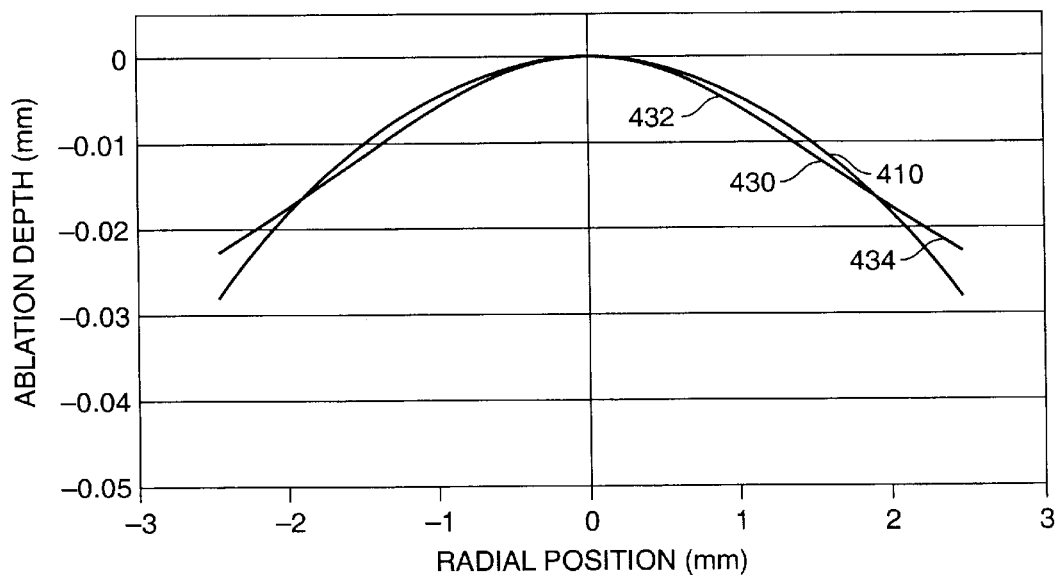
FIG. 11 illustrates an optical correction on a healed anterior corneal surface in comparison to an intended +3 D spherical optical correction.

The covering and healing of the ablated surface decrease the difference between the intended optical correction and the anterior corneal surface optical correction as illustrated in FIG. 11. A measured anterior corneal surface optical correction is plotted as a function of radial position over an ablated optical zone. The anterior optical correction 430 of the healed cornea more closely matches the intended +3 D spherical optical correction 410. However, errors between the intended optical correction 410 and the anterior surface optical correction 430 are still present. The central anterior optical correction 432 is over corrected compared to the intended +3 D spherical optical correction 410. This over correction of the central optical correction 432 is by about 25% relative to the intended +3 D optical correction, and corresponds to a 0.75 D near-vision correction at 2 mm. However, the peripheral anterior optical correction 434 is slightly under corrected relative to the intended +3 D optical correction. This correction of the peripheral anterior optical correction 434 appropriately provides distance vision correction. Therefore, the anterior optical correction 430 is multifocal and will provide some correction of presbyopia. This multifocal effect occurs because the ablated shape compensates for changes in corneal shape as the cornea heals. The peripheral ablated optical zone is overcorrected to provide distance vision on a healed cornea. The central optical zone is overcorrected to provide near-vision on the healed cornea. Commercially available corneal topography systems measure healed anterior corneal surfaces. Examples of such systems include the Atlas Corneal Topography System™ available from Humphrey Instruments of San Leandro, Calif. and the PAR CTS System™ available from PAR Vision Systems Corporation of New Hartford, N.Y.

Figure 12:
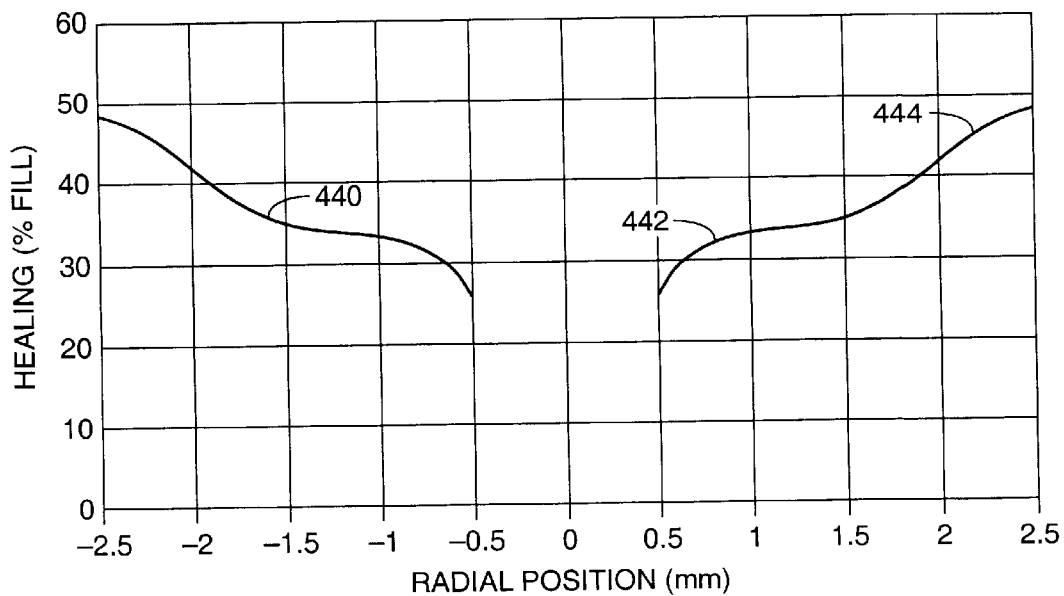
FIG. 12 illustrates the effect of covering and healing over an ablated optical zone.

The effect of the covering and corneal healing of an ablated optical zone is illustrated in FIG. 12. This figure illustrates the difference in shape between an ablated shape and the final anterior optical correction on the anterior surface of the cornea. This difference in shape is described as a healing-induced change 440 shown in FIG. 12. The healing-induced change 440 is illustrated for a patient treated for +3 D of hyperopia. The ablated shape is partially filled in by covering and healing to form the anterior optical correction. However, this partial filling is not constant over the ablated optical zone. The center of the ablated optical zone shows less filling than the peripheral optical zone. The peripheral optical zone is filled in by about 50% while the central optical zone is filled in by about 30%. A peripheral filling 444 is greater than a central filling 442. Proximity to the ablated transition zone causes the peripheral optical surface to be a different shape than the underlying ablated peripheral optical zone. However, the anterior central optical surface is distant from the ablated transition zone. Therefore, the shape of the anterior central optical surface more closely matches the shape of the ablated central optical zone. With the above differential healing, an optical zone ablated to a substantially spherical shape for correcting hyperopia will heal to an aspheric shape that corrects for presbyopia.

Figure 13:
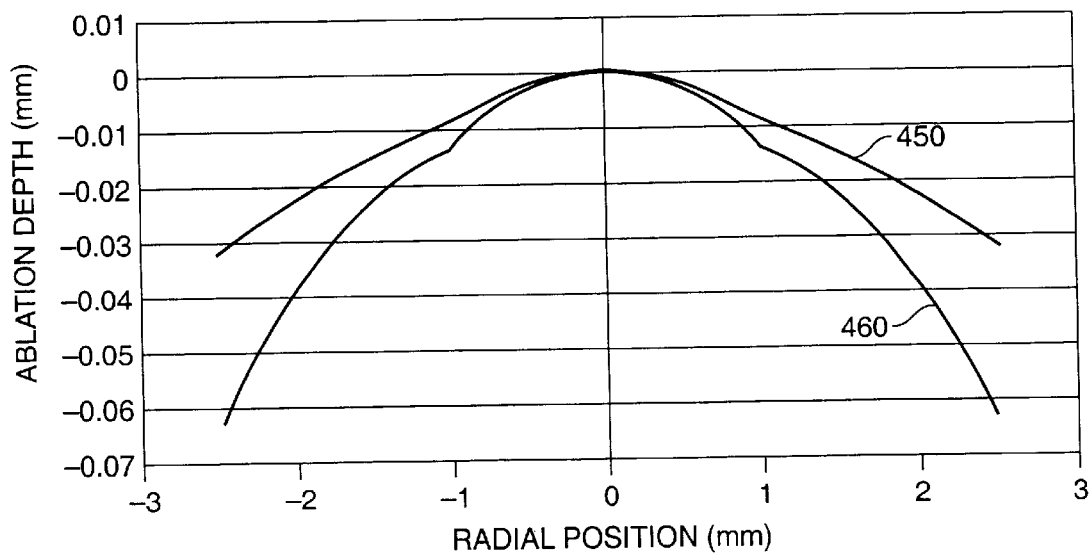
FIG. 13 illustrates an initial ablated shape derived from a desired shape and a healing-induced change.

By estimating a healing-induced change, an initial ablated surface shape may be derived from a desired anterior corneal surface shape and a healing-induced change as illustrated in FIG. 13. For example, consider a desired anterior surface correction 450 that corrects for +3 D of hyperopia and corrects for presbyopia with a central zone providing +3 D of near-vision correction. The desired anterior surface correction 450 is also illustrated in FIG. 13. An initial ablated surface shape 460 is calculated from the healing-induced change 440 and the desired anterior surface correction 450. The initial ablated shape 460 for the desired anterior surface correction 450 is illustrated in FIG. 13. The initial ablated shape 460 is overcorrected relative to the desired anterior surface correction. The initial ablated shape 460 is calculated by multiplying the desired anterior surface correction 450 by the ratio of the ablated shape 420 to the healed shape 430. A processor may be used to generate the ablated shape in response to the desired correction input by the system operator, typically making use of the embedded computer of the laser workstation, the PC workstation, and/or the programming and hardware of an external computer.

Figure 14:
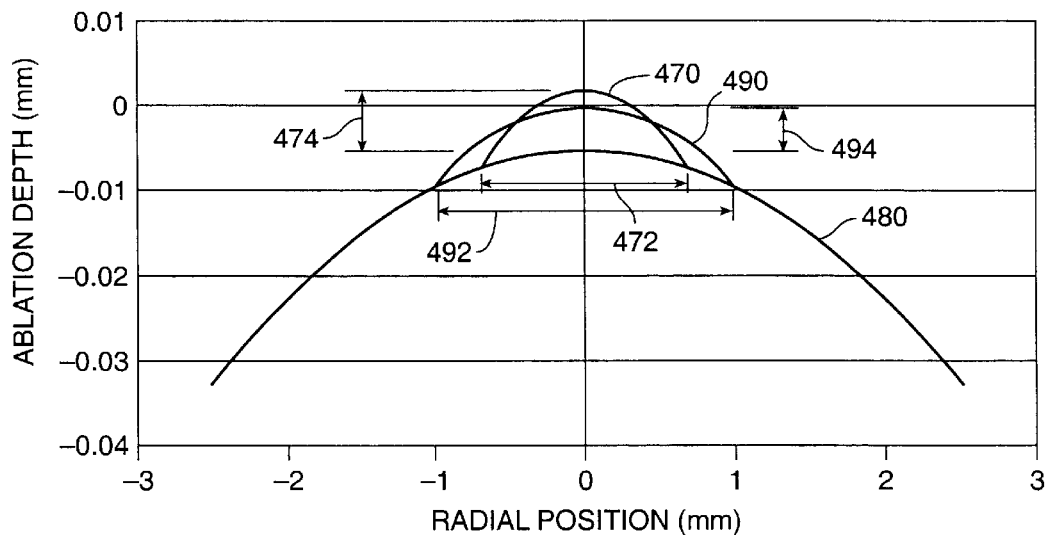
FIG. 14 illustrates overcorrecting and restricting an ablated surface shape relative to a desired anterior surface correction.

The ablated shape may be restricted or reduce relative to a desired anterior surface correction to obtain the desired anterior surface correction. The diameter of the relative restriction is between about 0.1 and 2 mm, preferably between about 0.2 and 1 mm and is ideally between about 0.3 and 0.7 mm. In an exemplary embodiment this restriction is about 0.5 mm as illustrated in FIG. 14. After covering an ablated corneal surface feature (such as a presbyopia correction) and allowing healing of a cornea, an anterior surface correction may extend beyond the initial ablated dimensions of the ablated surface feature. Ablated central zone 470 on reference 480 includes dimension 472 across the central ablated zone. Ablated central zone 470 also includes elevation 474 relative to the reference 480. Reference 480 may be any suitable reference such as a spherical reference surface on an anterior optical surface or an ablated surface. Covering of ablated central zone 470 and healing of the cornea will form a central anterior optical surface 490. Central anterior optical surface 490 includes dimension 492 across the central anterior optical surface and elevation 494 relative to reference 480. A 1.5 mm dimension 472 across the ablated central zone 470 will typically extend to a 2 mm dimension 492 across the central anterior optical surface 490. Therefore, to form a 2 mm central anterior optical surface, the ablated central zone is preferably restricted by a relative amount of about 0.5 mm. Also, it may be desirable to increase the elevation 474 of the ablated feature by a relative amount as illustrated above. For example, an ablation intended to produce a 4 um surface elevation 494 relative to a reference 480 on the anterior surface of a healed cornea may be over ablated as an 8 um surface elevation 474 relative to a reference 480. This overcorrecting of the ablated feature is by a relative amount of 4 um. Relative over-correction ranges from about 1 to 25 um. A desired final 2 mm diameter zone on an anterior surface to correct for near-vision with 3 D might typically have an elevation of about 4 um. To correct presbyopia using such a healed shape (in other words, to produce a central zone having a diameter of about 2 mm and an elevation of about 4 um on the anterior surface of a healed cornea), a central ablation zone having a restricted diameter of about 1.5 mm and an overcorrected elevation of about 8 um is ablated onto an exposed surface of the cornea. Although the term "diameter" is used to indicate a lateral dimension of these features (and in general in this application), it should be understood that the features need not necessarily be circular.

Figure 15:
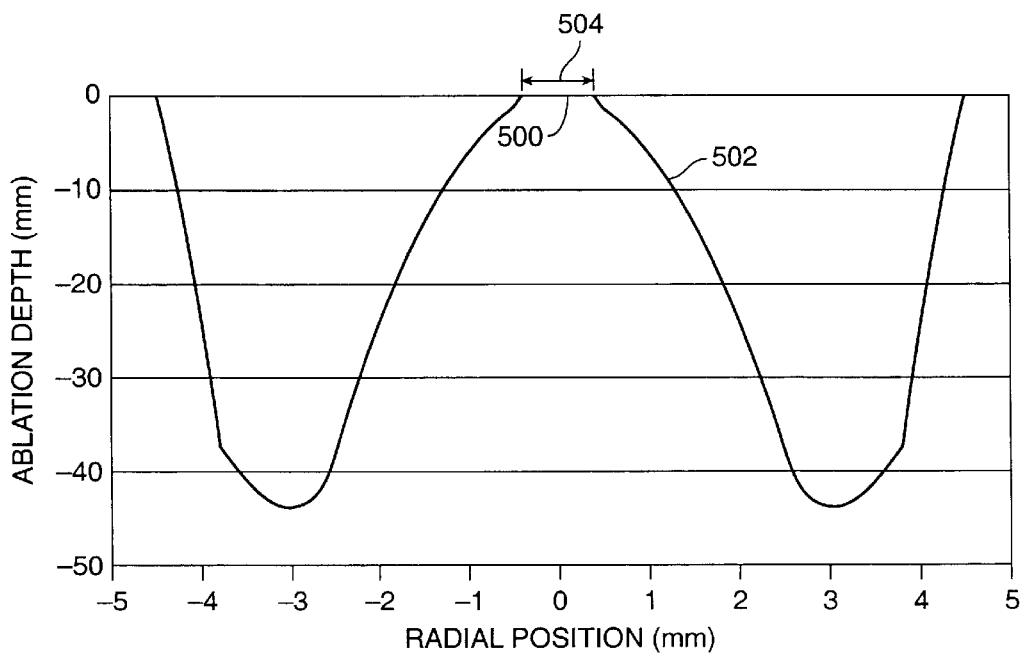
FIG. 15 illustrates a small untreated zone centered on the optical zone of an ablated surface.

In some instances, it may be desirable to treat presbyopia by leaving a central region of the optical zone untreated as illustrated in FIG. 15. A small untreated zone 500 centered on the optical zone 502 of an ablated cornea has a dimension 504 across the untreated zone. The untreated zone 504 is smoothed by covering and healing of the cornea and contributes to the formation of a central anterior optical surface that corrects presbyopia.

The above techniques can be used to calculate initial ablation shapes for treating conditions besides hyperopia and presbyopia. These techniques may be used to calculate the initial ablation shapes used to treat astigmatism, myopia and irregular refractive aberrations of the eye. For example, the higher order aberration terms of an irregular refractive aberration may be over corrected on an ablated corneal surface to form an anterior surface on a healed cornea with a desired optical correction of the higher order aberrations.

The above technique of making a multifocal optical correction on the anterior surface of the cornea can be applied to both eyes of a patient to provide an improved correction of presbyopia with binocular vision. The correction of presbyopia preferably covers about a 3 D range. However, with binocular vision this approximately 3 D range of presbyopia correction may be treated by treating each eye with a multifocal optical correction having less than the full 3 D range of presbyopia correction. In this case, the average refraction of each of the two eyes is different to provide clear vision over the full 3 D range. A first eye is corrected for near-vision, and a second eye is corrected for distance vision. The multifocal anterior optical surface provides improved focus for objects intermediate to near and far-vision. For example, one eye is treated to have an average refraction of −0.75 D with a 1.5 D multifocal range of focus. This eye has an effective focus from 0 to −1.5 D. The other eye is treated to have an average refraction of about −2.25 D with a 1.5 D multifocal range of focus. This eye has an effective focus from about −1.5 D to −3 D. The effective range of focus of the two eyes combined is about 3 D. The multifocal range on each eye varies between about 0.5 and 2.0 D, and is preferably between about 1.0 and 1.5 D. The difference between the average refraction of the two eyes varies between about 0.5 and 2.5 D, and is preferably between about 1 and 2 D.

While the above provides a full and complete disclosure of the preferred embodiments of the invention, various modifications, alternate constructions and equivalents may be employed as desired. For example, while the invention has been described with specific reference to the system of FIGS. 4 through 9, other systems may be employed, as desired. Further, lasers of other appropriate wavelengths than laser 28 may be used, if desired and effective. Also, laser systems which operate on the principle of thermal ablations, such as lasers having wavelengths lying in the infrared portion of the electromagnetic spectrum, may be used to implement the invention. In addition, while the radial and angular positioning of the profiled beam is accomplished with imaging lens 51 in the preferred embodiment, other optical scanning elements—such as rotating mirrors and prisms—may be employed, if desired. Therefore, the above description and illustrations should not be construed as limiting the invention, which is defined by the appended claims.

What is claimed is:

1. A laser eye surgery method comprising:
   determining an initial ablated shape for a cornea of an eye wherein the initial ablated shape differs significantly from a desired healed anterior surface shape which is multifocal and substantially corrects for presbyopia; and
   selectively ablating corneal tissue from the eye having an uncorrected surface shape so as to produce the initial ablated shape on an exposed surface of the cornea of the eye, the cornea then healing to transition from the initial ablated shape to the desired healed anterior surface shape so as to substantially correct the presbyopia.

2. The method of claim 1, wherein the initial ablated shape comprises a central ablated zone for near-vision and a peripheral ablated zone for distance vision and the healed anterior surface shape comprises a central anterior surface for near-vision and a peripheral anterior surface for distance vision.

3. The method of claim 2, further comprising overcorrecting the central ablated zone relative to the central anterior surface.

4. The method of claim 3, wherein the overcorrecting step comprises a relative amount from about 1 to 25 um.

5. The method of claim 2, further comprising restricting a dimension across the central ablated zone relative to the central anterior surface.

6. The method of claim 5, wherein the restricting step comprises a relative amount from about 0.1 to 2.0 mm.

7. The method of claim 2, wherein the peripheral anterior surface is a different shape than the peripheral ablated zone and the shape of to central anterior surface more closely matching the shape of the central ablated zone.

8. The method of claim 7, wherein the ablating step further comprises ablating a transition zone and the peripheral optical surface is proximal to the transition zone and the central optical surface is distant from the transition zone.

9. The method of claim 1, further comprising calculating a desired anterior surface shape, estimating a healing-induced change in the anterior surface, and deriving the initial ablated surface shape from the desired shape and the healing change prior to the selectively removing step.

10. The method of claim 9, wherein the initial ablated shape comprises a central ablated zone for near-vision and a peripheral ablated zone for distance vision and the healed anterior surface shape comprises a central anterior surface for near-vision and a peripheral anterior surface for distance vision.

11. The method of claim 10, farther comprising overcorrecting the central ablated zone relative to the central anterior surface.

12. The method of claim 11, wherein the overcorrecting step comprises a relative amount from about 1 to 25 um.

13. The method of claim 10, further comprising restricting a dimension across the central ablated zone relative to the central anterior surface.

14. The method of claim 13, wherein the restricting step comprises a relative amount from about 0.1 to 2.0 mm.

15. The method of claim 14, wherein the ablating step removes a portion of the cornea so as to simultaneously mitigate presbyopia of the eye.

16. The method as in claim 1, wherein healing comprises covering of the cornea by a new epithelial layer.

17. The method as in claim 1, wherein healing comprises covering of the cornea by a repositioned anterior flap of the corneal tissue.

18. The method as in claim 1, wherein the desired healed anterior surface shape additionally substantially corrects a refractive error of the eye.

19. The method as in claim 18, wherein the refractive error is selected from the group consisting of myopia, hyperopia, astigmatism, and irregular aberration.

20. The method am claim 1, further comprising providing a profiled beam with a center, and wherein selectively ablating comprises controlling with a computer the position of center over the cornea and creating a plurality of successive laser beam pulses wherein the positions of the plurality are determined by a laser treatment table.

21. The method as in claim 20, wherein the treatment table is scaled to a dimension of a pupil.

22. A laser eye surgery method comprising:

selectively ablating corneal tissue from an eye having a first refractive error so as to substantially correct the first refractive error, the first refractive error selected from the group consisting of myopia, hyperopia, astigmatism and irregular aberration, wherein healing of the eye from the ablating step simultaneously mitigates presbyopia of the eye.

23. The method as in claim 22, wherein healing comprises covering of the cornea by a new epithelial layer.

24. The method as in claim 22, wherein healing comprises covering of the cornea by a repositioned anterior flap of the corneal tissue.

25. The method as in claim 22, further comprising providing a profiled beam with a center, and wherein selectively ablating comprises controlling with a computer the position of the center over the cornea and creating a plurality of successive laser beam pulses wherein the positions of the plurality are determined by a laser treatment table.

26. The method as in claim 25, wherein the treatment table is scaled to a dimension of a pupil.

27. An ophthalmic surgery system for performing selective ablation of an exposed corneal surface of an eye to create a desired aspheric shape for correcting presbyopia on the anterior optical surface of a healed cornea, system comprising:

(i) means for directing a laser beam along a path;
(ii) means for profiling said beam to produce a profiled beam with a center;
(iii) means for displacing the center of the profiled beam over an area of the corneal surface; and
(iv) a computer for controlling the position of the center over the area and creating a plurality of successive laser beam pulses wherein the positions of the plurality are determined by a laser treatment table, the laser treatment table for ablating the exposed surface to form an ablated optical zone that is a different shape than the shape of the anterior optical surface.

28. The laser system of claim 27, wherein the treatment table is scaled to a dimension of a pupil.

29. The laser system of claim 27, wherein the ablated optical zone is user selectable.

30. The laser system of claim 27, wherein the ablated optical zone comprises a zone corrected for near-vision, and the zone corrected for near-vision is scaled to a dimension of a pupil.

31. The laser system of claim 27, wherein the ablated optical zone comprises an central zone for near-vision and the anterior optical surface comprises a central optical surface for near-vision, the laser treatment table over correcting the central zone relative to the central surface.

32. The laser system of claim 27, wherein the ablated optical zone comprises a central zone far near-vision and the anterior optical surface comprises a central optical surface for near-vision, the laser treatment table restricting a dimension across the central zone relative to the central surface.

33. An ophthalmic surgery system for performing selective ablation of an exposed corneal surface of an eye to create a desired aspheric shape for correcting presbyopia on the anterior optical surface of a healed cornea, the anterior optical surface comprising a central optical surface for near-vision, the system comprising:

(i) means for directing a laser beam along a path;
(ii) means for profiling said beam to produce a profiled beam with a center;
(iii) means for displacing the center of the profiled beam over an area of the corneal surface; and
(iv) a computer for controlling the position of the center over the area and creating a plurality of successive laser beam pulses wherein the positions of the plurality are determined by a laser treatment table, the laser treatment table for ablating the exposed surface to form an ablated optical zone comprising a zone corrected for near-vision, the optical zone being user selectable and a different shape than the shape of the anterior optical surface, the laser treatment table being scaled to a dimension of a pupil and over correcting the central zone relative to the central surface, the laser treatment table further restricting a dimension across the central zone relative to the central surface.

34. An ophthalmic surgery system for performing selective ablation of an exposed corneal surface of an eye to create a desired aspheric shape for correcting presbyopia on the anterior optical surface of a heated cornea, the system comprising:

(i) means for directing a laser beam along a path;
(ii) means for profiling said beam to produce a profiled beam with a center;
(iii) means for displacing the center of the profiled beam over an area of the corneal surface; and
(iv) a computer for controlling the position of the center over the area and creating a plurality of successive laser beam pulses wherein the positions of the plurality are determined by a laser treatment table, the laser treatment table being scaled to a dimension of pupil.

35. An ophthalmic surgery system for performing selective ablation of an exposed corneal surface of an eye to create a desired aspheric shape for correcting presbyopia on the anterior optical surface of a healed cornea, the system comprising:

(i) means for directing a laser beam along a path;
(ii) means for profiling said beam to produce a profiled beam with a center;

(iii) means for displacing the center of the profiled beam over an area of the corneal surface; and (iv) a computer for controlling the position of the center over the area and creating a plurality of successive laser beam pulses wherein the positions of the plurality are determined by a laser treatment table, the laser treatment table providing for the simultaneous correction of presbyopia and a refractive error selected from the group consisting of myopia, hyperopia, astigmatism and irregular refractive aberrations.

* * * * *